United States Patent
Petrikovics et al.

(10) Patent No.: US 10,238,609 B2
(45) Date of Patent: Mar. 26, 2019

(54) CYANIDE ANTIDOTE COMPOSITIONS AND METHODS OF USE

(71) Applicant: Sam Houston State University, Huntsville, TX (US)

(72) Inventors: Ilona Petrikovics, Huntsville, TX (US); Csaba Jaszberenyi, Huntsville, TX (US)

(73) Assignee: Sam Houston State University, Huntsville, TX (US)

( * ) Notice: Subject to any disclaimer, the term of this patent is extended or adjusted under 35 U.S.C. 154(b) by 0 days.

(21) Appl. No.: 15/345,573

(22) Filed: Nov. 8, 2016

(65) Prior Publication Data

US 2017/0071876 A1 Mar. 16, 2017

Related U.S. Application Data

(62) Division of application No. 14/066,924, filed on Oct. 30, 2013, now abandoned.

(60) Provisional application No. 61/720,114, filed on Oct. 30, 2012.

(51) Int. Cl.
*A61K 31/105* (2006.01)
*C07C 381/00* (2006.01)

(52) U.S. Cl.
CPC .......... *A61K 31/105* (2013.01); *C07C 381/00* (2013.01)

(58) Field of Classification Search
CPC .......................... A61K 31/105; C07C 381/00
See application file for complete search history.

(56) References Cited

U.S. PATENT DOCUMENTS 6,596,770 B2 * 7/2003 Lai ..................... A61K 31/4025
514/357

OTHER PUBLICATIONS

Mark A. Zottola, Keith Beigel, Sunil-Datta Soni, and Richard Lawrence, Disulfides as Cyanide Antidotes: Evidence for a New In Vivo Oxidative Pathway for Cyanide Detoxification, Chem. Res. Toxicol. 2009, 22, 1948-1953 (Year: 2009).*
Ilona Petrikovics, E. P. Cannon, W. D. McGuinn, L. Pei, L. Pu, L. E. Lindner, and J. L. Way, Cyanide Antagonism with Carrier Erythrocytes and Organic Thiosulfonates, Fundamental and Appued Toxicology 24, 86-93 (1995) (Year: 1995).*
Tadashi Okawara, Tetsuro Yamasaki, Kimitoshi Sato, Hiroyuki Miyazaki, and Mitsuru Furukawa, Reactions of p-Toluenesulfinic Acid with Dialkoxy or Diamino Sulfides and Disulfides, Chem. Pharm. Bull. 33 (12), 5225-5230 (1985) (Year: 1985).*

* cited by examiner

*Primary Examiner* — Sarah Pihonak
*Assistant Examiner* — Jason Deck
(74) *Attorney, Agent, or Firm* — Meyertons, Hood, Kivlin, Kowert & Goetzel, P.C.

(57) ABSTRACT

Cyanide antidote compositions and methods of use are described herein. A cyanide antidote composition may include a sulfur analog, sulfur analog derivative, or a pharmaceutically acceptable derivative of a sulfur analog.

11 Claims, 1 Drawing Sheet

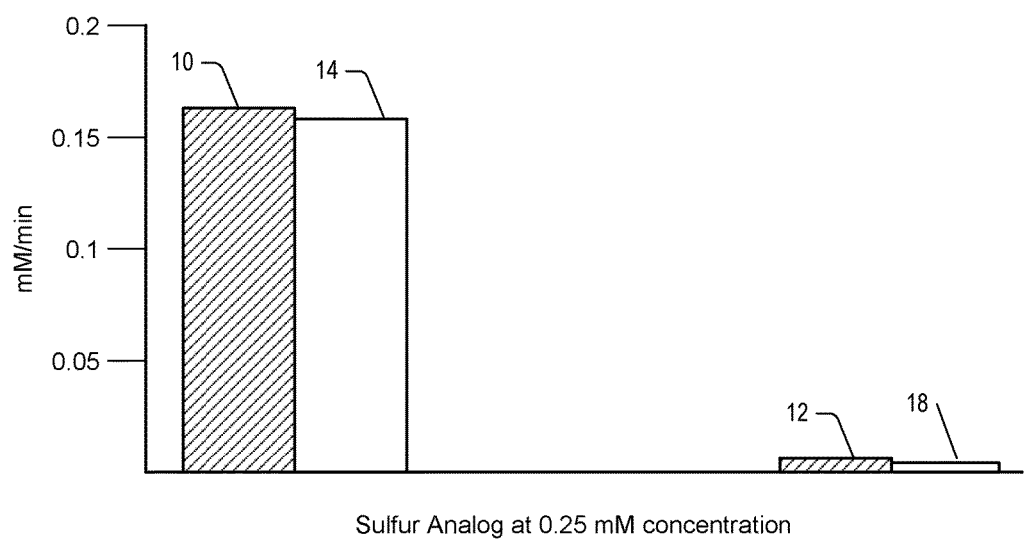

CYANIDE ANTIDOTE COMPOSITIONS AND METHODS OF USE

PRIORITY CLAIM

This application is a divisional application of U.S. patent application Ser. No. 14/066,924, filed Oct. 30, 2013 entitled "CYANIDE ANTIDOTE COMPOSITIONS AND METHODS OF USE" which claims the benefit of U.S. Provisional Application No. 61/720,114 filed on Oct. 30, 2012, both of which are incorporated herein by reference.

BACKGROUND

1. Field of the Invention

The present invention relates to antidotes for neurotoxins. More particularly, the invention relates to cyanide antidotes.

2. Brief Description of the Related Art

Neurotoxins damage or poison the central nervous system of mammals. An example of a neurotoxin is hydrogen cyanide. Inhalation or digestion of cyanide compounds may cause histotoxic hypoxia in tissue of the central nervous system as cyanide interferes with the performance of the cytochrome oxidase system thereby inhibiting the efficiency of oxygen transport to the tissues. Common cyanide compounds include hydrogen cyanide gas, cyanogen chloride gas, and crystalline solids such as potassium cyanide and sodium cyanide. The ease of delivery of these agents (especially gaseous cyanides) allow them to been used as an attack agent in chemical warfare.

Therapeutic attempts to counteract cyanide poisoning have been developed to inhibit the toxic effects of cyanide. For example, oxygen, sodium thiosulfate, amyl nitrite, sodium nitrite, 4-dimethylaminophenol, hydyoxocobalamin, dicobalt EDTA, garlic extracts, disulfides, sodium pyruvate, alpha-keto-glutaric acid, aqueous solutions of ferrous sulfate in a citric acid sodium carbonate solution have been for cyanide detoxification.

U.S. Pat. No. 4,565,311 to Sarnoff, which is incorporated herein by reference, describes as an antidote for cyanide poisoning injectable hydroxylamine hydrochloride. This is followed by treatment with thiosulfate. The hydroxylamine hydrochloride can also be employed as a respiratory stimulant in treating other illnesses.

Many disulfides have been tested as antidotes for cyanide intoxication. Zottola et al. in "Disulfides as Cyanide Antidotes: Evidence for a New In Vivo Oxidative Pathway for Cyanide Detoxification." Chemical Research Toxicology, 2009, 22, pp. 1948-1953, which is incorporated herein by reference, describes the conversion of cyanide to thiocyanate in the presence of the enzyme rhodanese. Rhodanese is an enzyme found primarily in the mitochondria. In a mammal, rhodanese is thought to be responsible for the conversion of cyanide to thiocyanate (SCN). Thiocyanate is then excreted by the kidney. Oxidized sulfur species such as sodium thiosulfate have been shown to be effective in vitro donors for rhodanese, however sodium thiosulfate in vivo efficacy is highly limited due to its limited cell penetration capability to reach the endogenous rhodanese. Thus, more effective sulfur analogs are desired.

Presently cyanide antidotes require intravenous injections with special trained personnel. Thus, the administration of the antidote is not efficient. As such, more efficient antidotal cyanide systems are desired.

SUMMARY

Cyanide antidote compositions and methods of use are described herein. In some embodiments, a cyanide antidote composition includes a sulfur analog, sulfur analog derivative, or pharmaceutically acceptable derivative of a sulfur analog, the sulfur analog has the structure:

where $R^1$ is S or $R^3$—$SO_2$—; $R^2$ is $R^4$—$SO_2$— or $R^5$; and n is 1 to 8.

$R^3$ and $R^4$ each independently are an alkyl moiety, an aryl moiety, or combinations thereof. In some embodiments, $R^3$ and $R^4$ are selected to have a chemical structure sufficient to increase lipophilic nature of the compound to enhance the penetration of the sulfur so that it reaches the endogenous rhodanese of the cell. In some embodiments, alkyl moieties include, but are not limited to, alkanes, alkenes, substituted alkanes, substituted alkenes, branched alkanes, branched alkenes or the like. Aryl moieties include benzene and/or substituted benzene. A benzene moiety may be substituted with one or more functional groups. Functional groups that may be present include, but are not limited to, alkyl, hydroxyl, carboxyl, amino, amide or the like.

$R^5$ is an alkyl moiety or an aryl moiety. $R^5$ is selected to have a chemical structure sufficient to increase lipophilic nature of the compound to enhance the penetration of the sulfur so that it reaches the endogenous rhodanese of the cell. Alkyl and aryl moieties include moieties as defined above for $R^3$ and $R^4$.

In some embodiments, a cyanide antidote composition includes a sulfur analog, sulfur analog derivative, or pharmaceutically acceptable derivative of a sulfur analog, the sulfur analog has the structure:

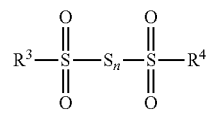

where $R^3$ and $R^4$ are each independently an alkyl moiety, an aryl moiety, or combinations thereof, and n ranges from 1 to 8.

In some embodiments, a method of treating the toxic effects of cyanide in a subject includes administrating to a subject who would benefit from such treatment a therapeutically effective amount of a sulfur analog, sulfur analog derivative, or pharmaceutically acceptable derivative of a sulfur analog sufficient to convert a sufficient amount of the cyanide to thiocyanate to detoxify the subject. The sulfur analog includes a disulfonyl sulfide.

In some embodiments, a method of treating the toxic effects of cyanide in a subject includes administrating to a subject who would benefit from such treatment a therapeutically effective amount of a sulfur analog, sulfur analog derivative, or pharmaceutically acceptable derivative of a sulfur analog sufficient to convert a sufficient amount of the cyanide to thiocyanate to detoxify the subject. The sulfur analog has the structure:

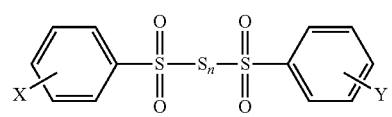

where X and Y are alkyl and/or aryl moieties, and n is at least 3.

In some embodiments, the sulfur analog has the structure:

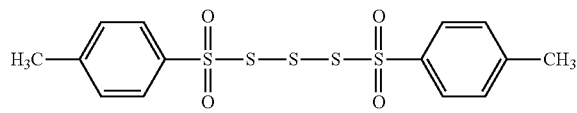

In some embodiments, a cyanide antidote composition includes a sulfur analog, sulfur donor derivative, or pharmaceutically acceptable derivative of a sulfur analog, at least one sulfur analog has a structure of: $S_nR^5$, where $R^5$ is an alkyl moiety, and aryl moiety, or a substituted aryl moiety and n is at least 3.

In some embodiments, a kit for administration of a cyanide antidote includes a sulfur analog, sulfur analog derivative, or pharmaceutically acceptable derivative of a sulfur analog. At least one of the sulfur analogs includes a disulfonyl sulfide.

BRIEF DESCRIPTION OF THE DRAWINGS

Features and advantages of the methods and apparatus of the present invention will be more fully appreciated by reference to the following detailed description of presently preferred but nonetheless illustrative embodiments in accordance with the present invention when taken in conjunction with the accompanying drawings in which:

FIG. 1 is a graphical depiction of various sulfur analogs at a known concentration versus rate of SCN formation.

While the invention is susceptible to various modifications and alternative forms, specific embodiments thereof are shown by way of example in the drawings and will herein be described in detail. The drawings may not be to scale. It should be understood that the drawings and detailed description thereto are not intended to limit the invention to the particular form disclosed, but to the contrary, the intention is to cover all modifications, equivalents and alternatives falling within the spirit and scope of the present invention as defined by the appended claims.

DETAILED DESCRIPTION

The enzymatic conversion of cyanide to thiocyanate requires a source of sulfane sulfur (a divalent ionized sulfur bonded to another sulfur atom) which is usually offered by thiosulfates or other biological compounds containing sulfane sulfur, like polythionates, thiosulfonates, and persulfides. Described herein are sulfur analogs, sulfur analog derivatives, or pharmaceutically acceptable derivatives of a sulfur analog, with superior reactivity, cell-penetrating capability and pharmacokinetic characteristics as compared to the presently clinically employed cyanide antidote, sodium thiosulfate.

It is to be understood that the present embodiments are not limited to particular compounds, methods or biological systems, which may, of course, vary. It is also to be understood that, as used in this specification and the appended claims, the singular forms "a", "an", and "the" include singular and plural referents unless the content clearly dictates otherwise. It is to be yet further understood that any terminology used herein is for the purpose of describing particular embodiments only, and is not intended to be limiting.

The terms used throughout this specification generally have their ordinary meanings in the art, within the context of the invention, and in the specific context where each term is used. Certain terms are discussed below or elsewhere in the specification, to provide additional guidance to the practitioner in describing the general embodiments of the invention, as well as how to make and use them. It will be readily appreciated that the same thing can be said in more than one way. Consequently, alternative language and synonyms may be used for any one or more of the terms discussed herein, nor is any special significance to be placed upon whether or not a term is elaborated or discussed in greater detail herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term.

As used herein, the term "tissue", when used in reference to a part of a body or of an organ, generally refers to an aggregation or collection of morphologically similar cells and associated accessory and support cells and intercellular matter, including extracellular matrix material, vascular supply, and fluids, acting together to perform specific functions in the body. There are generally four basic types of tissue in animals and humans including muscle, nerve, epithelial, and connective tissues.

As used herein, phrases such as "one or more additional compositions or medicaments suitable for the treatment of the toxic effects of cyanide in a subject," or more simply, "one or more additional compositions or medicaments," generally refer to a pharmaceutical composition that contains at least one pharmaceutically active compound that is used for the treatment of the toxic effects of cyanide in a subject, but which is distinct from the sulfur analogs or derivatives that form the basis of the present disclosure.

As used herein "cyanide intoxication" is to be understood to mean a medical condition that is characterized by cyanide interference with the performance of the cytochrome oxidase system thereby inhibiting the efficiency of oxygen transport to the tissues.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein the terms "administration," "administering," or the like, when used in the context of providing a pharmaceutical or nutraceutical composition to a subject generally refers to providing to the subject one or more pharmaceutical, "over-the-counter" (OTC) or nutraceutical compositions in combination with an appropriate delivery vehicle by any means such that the administered compound achieves one or more of the intended biological effects for which the compound was administered. By way of non-limiting example, a composition may be administered parenteral, subcutaneous, intravenous, intracoronary, rectal, intramuscular, intra-peritoneal, transdermal, or buccal routes of delivery. Alternatively, or concurrently, administration may be by the oral route. The dosage administered will be dependent upon the age, health, weight, and/or intoxicated state of the recipient, kind of concurrent treatment, if any, frequency of treatment, and/or the nature of the effect desired. The dosage of pharmacologically active compound that is administered will be dependent upon multiple factors, such as the age, health, weight, and/or disease state of the recipient, concurrent treatments, if any, the frequency of treatment, and/or the nature and magnitude of the biological effect that is desired.

As used herein, terms such as "pharmaceutical composition," "pharmaceutical formulation," "pharmaceutical preparation," or the like, generally refer to formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art. A pharmaceutical composition may be provided as sustained-release or timed-release formulations. Such formulations may release a bolus of a compound from the formulation at a desired time, or may ensure a relatively constant amount of the compound present in the dosage is released over a given period of time. Terms such as "sustained release," "controlled release," or "timed release" and the like are widely used in the pharmaceutical arts and are readily understood by a practitioner of ordinary skill in the art. Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, solvents and/or auxiliaries that are, typically, pharmacologically inert. It will be readily appreciated by an ordinary practitioner of the art that, included within the meaning of the term are pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

In some embodiments, the sulfur analogs may be chemically modified or immobilized to increase the lipophilic character of the sulfur analog. Increasing the lipophilic character of the sulfur analog may enhance the cell penetration of the sulfur analog. In some embodiment, the sulfur analogs are chemically modified to form pharmaceutically acceptable salts.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. Pharmaceutically acceptable acid addition salts of the compounds of the invention include salts derived from inorganic acids such as hydrochloric, nitric, phosphoric, sulfuric, hydrobromic, hydroiodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, butyrate, caprylate, isobutyrate, oxalate, malonate, succinate, sulfosalicylate, salicylate, suberate, sebacate, fumarate, maleate, laurate, mandelate, benzoate, chlorobenzoate, hydroxybenzoate, methylbenzoate, dinitrobenzoate, phthalate, benzenesulfonate, toluenesulfonate, phenylacetate, citrate, lactate, maleate, tartrate, embonate, stearate, hydroxynaphthoate, methanesulfonate, and the like. Also contemplated are the salts of amino acids such as arginate, gluconate, galacturonate, and the like; see, for example, Berge et al., "Pharmaceutical Salts," J. of Pharmaceutical Science, 1977; 66:1 19. The acid addition salts of the basic compounds are prepared by contacting the free base form with a sufficient amount of the desired acid to produce the salt in the conventional manner The free base form may be regenerated by contacting the salt form with a base, and isolating the free base in the conventional manner The free base forms differ from their respective salt forms somewhat in certain physical properties such as solubility in polar solvents, but otherwise the salts are equivalent to their respective free base for purposes of the present invention. Pharmaceutically acceptable base addition salts are formed with metals or amines, such as alkali and alkaline earth metal hydroxides, or of organic amines. Examples of metals used as cations are sodium, potassium, calcium, aluminum, magnesium, titanium, ammonium and the like. Examples of suitable amines are N,N'-dibenzylethylenediamine, chloroprocaine, choline, diethanolamine, ethylenediamine, N-methylglucamine, meglumine, guanidine, and procaine. The base addition salts of acidic compounds are prepared by contacting the free acid form with a sufficient amount of the desired base to produce the salt in the conventional manner The free acid form may be regenerated by contacting the salt form with an acid and isolating the free acid in a conventional manner The free acid forms differ from their respective salt forms somewhat in certain physical properties such as solubility in polar solvents, but otherwise the salts are equivalent to their respective free acid for purposes of the present invention. Lists of suitable salts are found in Remington's Pharmaceutical Sciences, 17th ed., Mack Publishing Company, Easton, Pa., 1985, p. 1418, the disclosure of which is hereby incorporated by reference. It is understood that the active compounds and their pharmaceutically acceptable salts mentioned can also be present, for example, in the form of their pharmaceutically acceptable solvates, in particular in the form of their hydrates.

As used herein the terms "subject" generally refers to a mammal, and in particular to a human.

The terms "in need of treatment," "in need thereof," "who would benefit from such treatment," or the like when used in the context of a subject being administered a pharmacologically active composition, generally refers to a judgment made by an appropriate healthcare provider that an individual or animal requires or will benefit from a specified treatment or medical intervention. Such judgments may be made based on a variety of factors that are in the realm of expertise of healthcare providers, but include knowledge that the individual or animal has been exposed to cyanide and that may be detoxified, ameliorated, or treated with the specified medical intervention.

The phrases "therapeutically effective amount" and "effective amount" are synonymous unless otherwise indicated, and mean an amount of a compound of the present invention that is sufficient to improve the condition, disease, or disorder being treated. Determination of a therapeutically effective amount, as well as other factors related to effective administration of a compound of the present invention to a patient in need of treatment, including dosage forms, routes of administration, and frequency of dosing, may depend upon the particulars of the condition that is encountered, including the patient and condition being treated, the severity of the condition in a particular patient, the particular compound being employed, the particular route of administration being employed, the frequency of dosing, and the particular formulation being employed. Determination of a therapeutically effective treatment regimen for a patient is within the level of ordinary skill in the medical or veterinarian arts. In clinical use, an effective amount may be the amount that is recommended by the U.S. Food and Drug Administration, or an equivalent foreign agency. The amount of active ingredient that can be combined with the carrier materials to produce a single dosage form varies depending upon the mammalian host treated and the particular mode of administration.

The term "pharmacologically inert," as used herein, generally refers to a compound, additive, binder, vehicle, and the like, that is substantially free of any pharmacologic or "drug-like" activity.

A "pharmaceutically or nutraceutically acceptable formulation," as used herein, generally refers to a non-toxic formulation containing a predetermined dosage of a pharmaceutical and/or nutraceutical composition, wherein the dosage of the pharmaceutical and/or nutraceutical composition is adequate to achieve a desired biological outcome. The meaning of the term may generally include an appropriate delivery vehicle that is suitable for properly delivering the pharmaceutical composition in order to achieve the desired biological outcome.

A method of treating cyanide intoxication in a subject includes administering to a subject who would benefit from such treatment a therapeutically effective amount of a sulfur analog, sulfur analog derivative, or pharmaceutically acceptable derivative of a sulfur analog, at least one sulfur analog sufficient to convert cyanide ion in the subject to SCN. The SCN may be excreted by the subject's kidney system.

In some embodiments, a sulfur analog, including pharmaceutically acceptable salts thereof, in applications directed to treating cyanide intoxication in a subject may include administrating to a subject having need for such treatment a therapeutically effective amount of a pharmaceutically acceptable composition that include a sulfur analog, sulfur analog derivative, or pharmaceutically acceptable derivative of a sulfur analog described herein.

In some embodiments, uses of sulfur analogs, including pharmaceutically acceptable salts thereof, directed to treating cyanide intoxication in a subject may include the preparation of pharmaceutical compositions for use with additional compounds which, when co-administered, act synergistically to convert cyanide to thiocyanate in a subject. Examples of additional compounds include liposomes and/or dendrimeric polymers. In some embodiments, the pharmaceutical composition includes but is not limited to, liposomes, dendrimeric polymers, microspheres, or combinations thereof.

One or more of the additional compounds suitable for the treatment of the cyanide intoxication presently contemplated may be formulated as a separate pharmaceutical composition to be administered in conjunction with the subject sulfur analogs as part of a therapeutic regimen, or may be formulated in a single preparation together with the sulfur analog. A combined composition may be administered orally, parenterally, by inhalation spray, rectally, or topically in dosage unit formulations containing conventional nontoxic pharmaceutically acceptable carriers, adjuvants, and vehicles as desired. Topical administration may involve the use of transdermal administration such as transdermal patches or iontophoresis devices. The term parenteral generally embraces non-oral routes of administration, including but not limited to, subcutaneous injections, intravenous, intramuscular, intrasternal injection, or infusion techniques.

Therapeutic kits that include sulfur analogs, either alone or in combination with an additional composition suitable for the treatment of the medical condition are also contemplated herein. Such kits will generally contain, in suitable container means, a pharmaceutically acceptable formulation of at least one sulfur analog compound. The kits also may contain other pharmaceutically acceptable formulations, such as those containing components to target the sulfur analog to distinct regions of a patient where treatment is needed, for example, those additional medicaments as described above.

The kits may have a single container means that contains the sulfur analog compounds, with or without any additional compositions or medicaments, or they may have distinct container means for each desired composition. When the components of the kit are provided in one or more liquid solutions, the liquid solution is an aqueous solution, with a sterile buffered aqueous solution being particularly preferred. However, the components of the kit may be provided as dried powder(s). When reagents or components are provided as a dry powder, the powder can be reconstituted by the addition of a suitable solvent. It is envisioned that the solvent also may be provided in another container means. The container means of the kit will generally include at least one vial, test tube, flask, bottle, syringe or other container means, into which the medically active agent(s), and any other desired agent, may be placed and, preferably, suitably aliquoted. Where additional components are included, the kit will also generally contain a second vial or other container into which these are placed, enabling the administration of separated designed doses. The kits also may comprise a second/third container means for containing a sterile, pharmaceutically acceptable buffer or other diluent.

The kits also may contain a means by which to administer the pharmaceutical compositions to an animal or patient, e.g., one or more needles or syringes, or even an eye dropper, pipette, or other such like apparatus, from which the formulation may be injected into the animal. The kits of the present invention will also typically include a means for containing the vials, or such like, and other component, in close confinement for commercial sale, such as, e.g., injection or blow-molded plastic containers into which the desired vials and other apparatus are placed and retained.

The kit may include protective clothing. Examples of protective clothing include gloves, safety glasses, gas mask, and the like.

In some embodiments, a composition may include a sulfur analog, optionally in combination with one or more additional compounds suitable for the treatment of cyanide intoxication. Sulfur analogs suitable for use in accordance with the treatment of cyanide intoxication include sulfur analogs having sufficient sulfur moieties to convert the cyanide to thiocyanate. At least one sulfur analog includes from at least 3 to 8, from 4 to 6, or from 5 to 7 sulfur atoms. The sulfur analog may include one or more aromatic compounds, one or more sulfonyl compounds, and one or more alkyl groups.

In an embodiment, a sulfur analog has the general composition:

$$R^1-S_n-R^2 \quad \quad (I)$$

where $R^1$ is S or $R^3$—$SO_2$—; $R^2$ is $R^4$—$SO_2$— or $R^5$; and n is 1 to 8.

$R^3$ and $R^4$ each independently are an alkyl moiety, an aryl moiety, or combinations thereof. In some embodiments, $R^3$ and $R^4$ are selected to have a chemical structure sufficient to increase lipophilic nature of the compound to enhance the penetration of the sulfur so that it reaches the endogenous rhodanese of the cell. In some embodiments, alkyl moieties include, but are not limited to, alkanes, alkenes, substituted alkanes, substituted alkenes, branched alkanes, branched alkenes or the like. Aryl moieties include benzene and/or substituted benzene. A benzene moiety may be substituted with one or more functional groups. Functional groups that may be present include, but are not limited to, alkyl, hydroxyl, carboxyl, amino, amide or the like.

$R^5$ is an alkyl moiety or an aryl moiety. $R^5$ is selected to have a chemical structure sufficient to increase lipophilic nature of the compound to enhance the penetration of the sulfur so that it reaches the endogenous rhodanese of the cell. Alkyl and aryl moieties include moieties as defined above for $R^3$ and $R^4$.

In some embodiments, the sulfur analog is a disulfonyl sulfide having a structure of:

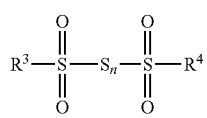

(II)

where $R^3$ and $R^4$ are alkyl moieties, aryl moieties, or combinations thereof, as defined above, and n ranges from 1 to 8, from 2 to 6, or from 3 to 5. In an embodiment, $R^3$ and $R^4$ are substituted aryl compounds and n is 3. In another embodiment, $R^3$ is an substituted alkene (e.g., an allyl group) and $R^4$ is an aryl moiety.

In some embodiments, $R^3$ and $R^4$ are substituted aryl moieties. For example, the sulfur analog may have the structure of:

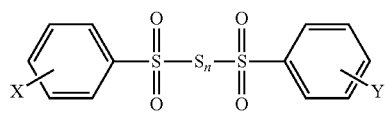

(III)

where X and Y are alkyl, OH, $NH_2$, $NHCO_2R^6$, and/or $CO_2R^6$, where $R^6$ is hydrogen, alkyl or aryl, or amino; and n ranges from 1 to 8, from 2 to 6, or from 3 to 5.

In a specific embodiment, the sulfur analog has a structure of:

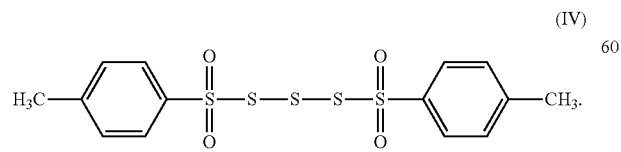

(IV)

In some embodiments, the sulfur analog may be an alkyl sulfide. For example, the sulfur analog may have a structure of: $S_nR^5$, where $R^5$ is an alkyl moiety or an aryl moiety as defined above for $R^3$ and $R^4$, and n is at least 3.

In some embodiments, the sulfur may be aryl sulfonyl sulfide having the structure of:

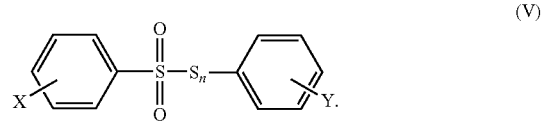

(V)

where X and Y are alkyl, OH, $NH_2$, $NHCO_2R^6$, and/or $CO_2R^6$, where $R^6$ is hydrogen, alkyl or aryl, or amino; and n ranges from 1 to 8, from 2 to 6, or from 3 to 5.

In vitro testing of sodium thiosulfate has been shown to convert cyanide to thiocyanate (SCN). It has been unexpectedly found that aromatic trisulfides described herein produce enhanced in in vitro conversion of cyanide to thiocyanate efficacy.

In vitro testing of Compound IV and sodium thiosulfate was performed in the presence and absence of the enzyme rhodanese to determine the efficacy of Compound IV as compared to sodium thiosulfate in the conversion of sodium cyanide to SCN. It was unexpectedly found that sodium cyanide was converted to SCN least 10 times faster in the presence of Compound IV than in the presence sodium thiosulfate.

Non-limiting examples of sulfur analog testing with the enzyme rhodanese are described herein.

EXAMPLE

Assay Protocol

Assay Materials

A 0.125 mM solution of the sulfur analog in a solution of 0.5 mL methylene chloride and 0.1 mL of ethanol was prepared. A portion of this solution (0.2 ml) was used for the assay. (For thiosulfate as control sulfur donor, 10 mM phosphate buffer (pH=7.4) was used as solvent).

Rhodanese solution (1 mg solid /ml; 119 Units/mg solid) in 10 mM PBS, pH=7.4 was prepared. (Rhodanese activity of the solution: 119 Units/ml)

A 250 mM potassium cyanide (KCN) solution was prepared.

A 10 mM phosphate buffer in 0.9% saline (PBS) pH 7.4 was prepared.

A 15.2% formaldehyde solution (75 ml water+50 ml formaldehyde (38%)) was prepared.

A ferric nitrate reagent was prepared as follows: Fe(NO3) 3×9 $H_2O$ (33.33 g) was dissolved completely in nitric acid (66.6 mL nitric acid (65%)). The volume of the ferric nitrate solution determined, and then the ferric nitrate solution was added to sufficient water to make a final volume of 500 mL.

Assay Procedure

The assay to determine the in vitro efficacy of sulfur analogs in the conversion of potassium cyanide (KCN) to SCN was determined as follows.

A separate tube with 1 ml water was used as control.

In a test tube, the components were placed in the following order: 1) 0.2 ml of sulfur analog solution prepared freshly (0.125 mM); 2) water; 3) Phosphate Buffer Saline (PBS); 4) KCN according to TABLE 1. A timer was set after adding the KCN was added. (When Rh was employed, it was added before the KCN).

TABLE 1

|  | No Rhodanese | Rhodanese |
|---|---|---|
| Water (mL) | 0.4 | 0.395 |
| PBS (mL) | 0.2 | 0.2 |
| KCN, 250 mL, (mL) | 0.2 | 0.2 |
| Sulfur analog, 0.125 mM (mL) | 0.2 | 0.2 |
| Rhodanese (1 mg/mL in 10 mM PBS) (119 units/mL) (μl) | 0 | 5 (0.595 Units of Rh) |

The sulfur analogs used were compound IV and sodium thiosulfate ($Na_2S_2O_3$).

The test tube was incubated for 5 minute.

0.5 ml of formaldehyde solution was added to all test tubes including the control.

1.5 ml of ferric nitrate solution was added to all tubes including control.

The color intensity was measured at the wavelength of 464 nm after 1 minute.

Formation of SCN was determined by measured by measuring the color intensity at 464 nm after 1 minute and correlating the intensity to a calibration curve. The calibration curve was prepared by making a series of solutions with known concentrations of SCN. The color intensity of the solutions were measured and plotted to show the relationship between concentration and absorbance.

Two sets of experiments were performed. The first set of experiments, the in vitro efficacy of Compound IV and sodium thiosulfate in the presence of rhodanese was compared. In the second of experiments, the in vitro efficacy of Compound IV and sodium thiosulfate were compared in the absence of rhodanese. The rate of conversion of potassium cyanide to SCN for each experiment is listed in TABLE 2.

TABLE 2

| Sulfur analog | Rhodanese present mM of SCN/min | No Rhodanese mM of SCN/min |
|---|---|---|
| Compound IV | 0.16 | 0.158 |
| Sodium thiosulfate | 0.005 | 0.0029 |
| Control | 0.0 | 0.0 |

A graphical representation of values in TABLE 2 is shown in FIG. 1. Data 10 is Compound IV in the presence of rhodanese. Data 12 is sodium thiosulfate in the presence of rhodanese. Data point 14 is Compound IV in the absence of rhodanese. Data point 16 is sodium thiosulfate in the absence of rhodanese.

As shown in TABLE 2 and FIG. 1, the in vitro efficacy of compound IV is at least a factor of 10 faster as compared to sodium thiosulfate.

is to be understood the invention is not limited to particular systems described which may, of course, vary. It is also to be understood that the terminology used herein is for the purpose of describing particular embodiments only, and is not intended to be limiting. As used in this specification, the singular forms "a", "an" and "the" include plural referents unless the content clearly indicates otherwise. Thus, for example, reference to "a core" includes a combination of two or more cores and reference to "a material" includes mixtures of materials.

In this patent, certain U.S. patents and U.S. patent applications have been incorporated by reference. The text of such U.S. patents and U.S. patent applications is, however, only incorporated by reference to the extent that no conflict exists between such text and the other statements and drawings set forth herein. In the event of such conflict, then any such conflicting text in such incorporated by reference U.S. patents and U.S. patent applications is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of treating cyanide intoxication in a subject, comprising:
administrating to a subject who would benefit from such treatment a therapeutically effective amount of a sulfur analog, or pharmaceutically acceptable derivative of a sulfur analog in an amount sufficient to convert at least some cyanide to thiocyanate to detoxify the subject, wherein the sulfur analog has the structure $$R^1\text{—}S_n\text{—}R^2 \qquad (I)$$

where $R^1$ is $R^3$—$SO_2$—; $R^2$ is $R^4$—$SO_2$— or $R^5$; and n is 1 to 8;
where $R^3$ is an alkyl moiety or an aryl moiety;
where $R^4$ is an alkyl moiety or an aryl moiety; and
$R^5$ is an alkyl moiety or an aryl moiety.

2. The method of claim 1, wherein the sulfur analog has the structure:

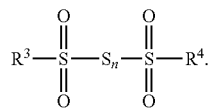

3. The method of claim 2, wherein $R^3$ and $R^4$ comprise aryl moieties and n is 1.

4. The method of claim 2, wherein $R^3$ and $R^4$ comprise one or more substituted aryl moieties.

5. The method of claim 1, wherein $R^3$ is an allyl moiety and $R^4$ is an aryl moiety.

6. The method of claim 1, wherein the sulfur analog has the structure:

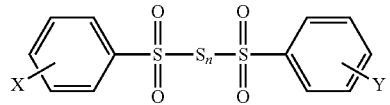

where X and Y are alkyl, OH, $NH_2$, $NHCO_2R^6$, and/or $CO_2R^6$, where $R^6$ is hydrogen, alkyl or aryl, or amino; and n ranges from 3 to 8.

7. The method of claim 1, wherein the sulfur analog has the structure:

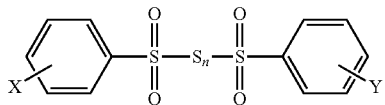

where X and Y are alkyl moieties.

8. The method of claim 1, wherein the sulfur analog has the structure:

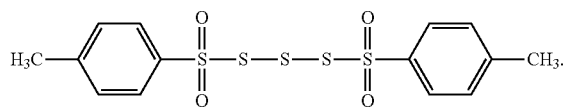 [SMILES: Cc1ccc(S(=O)(=O)SSSS(=O)(=O)c2ccc(C)cc2)cc1]

9. The method of claim 1, further comprising liposomes and/or dendrimeric polymers.

10. The method of claim 1, wherein the sulfur analog has the structure —$S_nR^5$, where $R^5$ is an alkyl moiety, or aryl moiety and n ranges from 3 to 8.

11. The method of claim 1, wherein the sulfur analog has the structure:

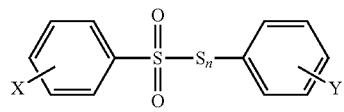

where X and Y are alkyl, OH, $NH_2$, $NHCO_2R^6$, and/or $CO_2R^6$, where $R^6$ is hydrogen, alkyl or aryl, or amino; and n ranges from 1 to 8.

* * * * *